United States Patent [19]

Fishman et al.

[11] Patent Number: 4,571,386

[45] Date of Patent: Feb. 18, 1986

[54] FELINE INFECTIOUS PERITONITIS VACCINE

[76] Inventors: Bernard Fishman, 7 Rowlands Close, Gillingham, Kent; Louise M. Hitchcock, 65 Kingswood Ave., Shortlands, Bromley, Kent; Kevin J. O'Reilly, Lambardes, Drakeley's Field, Milland, Near Liphook, Hants, all of England

[21] Appl. No.: 288,269

[22] Filed: Jul. 30, 1981

Related U.S. Application Data

[63] Continuation of Ser. No. 98,592, Nov. 29, 1979, abandoned.

[30] Foreign Application Priority Data

Nov. 30, 1978 [GB] United Kingdom ............... 46603/78

[51] Int. Cl.$^4$ ......................... C12N 7/00; A61K 39/12
[52] U.S. Cl. ..................................... 435/235; 424/89; 435/236; 435/237
[58] Field of Search ................... 424/89; 435/235–239

[56] References Cited

U.S. PATENT DOCUMENTS

| | | | |
|---|---|---|---|
| 3,293,130 | 12/1966 | Slater et al. | 424/89 |
| 3,520,972 | 7/1970 | Smith et al. | 424/89 |
| 3,709,782 | 1/1973 | Smith et al. | 435/237 |
| 3,892,627 | 7/1975 | Simons et al. | 435/237 |
| 3,937,812 | 2/1976 | Bittle et al. | 424/89 |
| 3,944,469 | 3/1976 | Bittle et al. | 435/237 |
| 4,031,204 | 6/1977 | Davis | 435/238 |
| 4,195,130 | 3/1980 | Hoshino et al. | 435/235 |
| 4,287,178 | 9/1981 | Bittle | 435/237 |
| 4,293,653 | 10/1981 | Horzinek et al. | 435/237 |
| 4,303,644 | 12/1981 | Davis | 435/237 |
| 4,312,947 | 1/1982 | Ackermann et al. | 435/235 |

*Primary Examiner*—Shep K. Rose
*Attorney, Agent, or Firm*—Donald Brown

[57] ABSTRACT

An attenuated strain of feline infectious peritonitis virus suitable for immunizing animals against feline infectious peritonitis (FIP) is prepared by serially passaging virulent FIP virus in susceptible cell cultures, and then combining it with a pharmaceutically acceptable carrier to form a vaccine.

3 Claims, No Drawings

FELINE INFECTIOUS PERITONITIS VACCINE

This is a continuation of application Ser. No. 098,592, filed Nov. 29, 1979, now abandoned.

This invention relates to an attenuated strain of feline infections peritonitis virus, hereinafter referred to as FIP virus, and to a method of producing such an attenuated strain. In a further aspect there is provided a vaccine for developing immunity to FIP in animals of the genus Felix.

Feline infectious peritonitis is an important disease of both domestic and wild Felidae because it is almost invariably fatal. The disease was first recognised in about 1950 and reported under the name chronic fibrinous peritonitis (*J.Amer. Vet.Med. Assoc.*, 144, 1409–1420, (1963)). Since then FIP has been diagnosed in North America, Europe, South Africa, Australasia and Japan. More recently the causative organism has been described as a coronalike virus (*Nature*, 266, 682, (1977)).

Animals which contract the disease become lethargic and inappetant. Fluid collects in the peritoneal cavity with the result that the abdomen becomes enlarged and the cat eventually dies in a jaundiced state. Whilst therapy and supportive treatment may prolong the course of the disease, all animals showing clinical signs eventually die, (*J.Amer. Vet. Med. Assoc.*, 154, 26–35, (1969)).

It has long been recognised that a vaccine is required to prevent FIP outbreaks (*J.Amer. Vet. Med. Assoc.*, 155, 1728–1733, (1969)), however, many attempts to isolate and grow the virus have failed. It has recently been reported that FIP virus has been grown in feline small intestine organ culture, (*The Cornell Veterinarian*, 68, 411–417, (1978)), but this is not a practical method for vaccine production, or for attenuating the virus.

It has now been found that a live attenuated strain of FIP virus can be prepared which stimulates serum antibody such as neutralising antibody in susceptible animals with very slight or no side effects. By electron microscopy, using negatively stained preparations, the virus morphologically resembles coronavirus and in particularly avian infectious bronchitis virus, hereinafter referred to as A.I.B.

FIP virus differs from A.I.B. virus in that it will not grow in the embryonating egg. However FIP virus is the only mammalian coronavirus, other than human coronavirus, that will grow in tissue culture and produce an obvious cytopathic effect, hereinafter referred to as CPE. In general human coronaviruses cause a slow and partial degeneration of the cell sheet whereas attenuated FIP virus completely destroys the monolayer culture in 48 to 72 hours.

According to the present invention in one aspect there is provided an attenuated strain of feline infectious peritonitis virus which stimulates the production of antibody in susceptible animals, without causing sumptoms characteristic of an FIP infection, which morphologically resembles a coronavirus and in particular the causative virus of A.I.B., whilst differing from A.I.B. virus in its growth properties in as much as it is capable of growing in mammalian tissue culture but not in embryonating eggs, and which on infecting tissue culture cells causes a characteristic CPE in which the cells produce irregular shapes when examined microscopically as wet preparations, and ultimately round up and/or become detached from the solid surface on which they are growing.

Members of the coronaviridae are essentially spherical in shape with a diameter of 80 to 160 nm, together with outstanding projections about 25 nm long, which give the viruses the appearance of possessing a halo or corona.

Such an attenuated strain of FIP virus may be prepared by serially passaging an isolate of virulent FIP virus in feline embryonic cell cultures, such as a cell line or cell strain, about 100 times, to yield a virus of reduced pathogenicity, but the infectivity and immunogenicity of which are retained.

According to a second aspect of the invention there is provided a method of attenuating a virulent feline infectious peritonitis virus comprising serially passaging an isolate of virulent FIP virus in feline embryonic cell cultures as defined above about 100 times, and optionally propagating the attenuated virus in a susceptible cell culture to provide enough virus for a vaccine.

Virulent FIP virus may be isolated from the peritoneal fluid, blood, urine and various organs of a cat suffering from the disease. In the case of the peritoneal fluid, and urine, the infected fluid may be inoculated directly on to the selected cell cultures. For isolating virus from the blood the infected animal may be bled from the jugular or any other suitable vein. The sample is subsequently allowed to clot; the clot is then removed and triturated for example in a pestle and mortar, and resuspended in a suitable medium, such as phosphate buffered saline. The suspension is then centrifuged to remove gross tissue debris, the supernatant fluid is removed and used to inoculate cell cultures. Virus may also be obtained from such organs as the liver, spleen or omentum; the procedure for preparing the virus for inoculation into cultures is essentially similar to that for the clotted blood, in that the organ is triturated, resuspended, followed by centrifugation and removal of the supernatant.

Feline embryonic cell cultures suitable for serially passaging the virulent virus may be derived from such organs as lung, kidney, heart, liver or gut of a member of the genus Felix, or a mixture thereof, or alternatively from the skin, muscle, amnion (placenta) or tongue. The cell cultures may be prepared from the various parts of a feline embryo, or even the whole embryo, by the method described in British Pat. Nos. 1 177 635 and 1 286 250 and also in the *J. Hygiene,* 67, (1969), 115-124. The former patent describes a method for preparing diploid cell strains, whilst the latter describes the preparation of heteroploid cell lines. The methods comprise taking the embryo, or the required part of it, and disaggregating it mechanically or enzymatically. The resulting cell suspension is transferred into suitable containers holding a nutrient medium suitable for culturing cells, and then incubating at 32° to 39° C. To facilitate subculturing it is customary to treat the confluent sheets of cells with trypsin and an innocuous chelating agent, before each transfer into fresh medium. Alternatively primary feline cell cultures may be used for growing FIP virus, and these are prepared by techniques well known in the art, and as described in any virological textbook.

The isolated virulent FIP virus may be propagated by inoculating a confluent monolayer or sheet of the selected feline embryonic cells with the isolate from the infected animal, followed by incubation at 35° C. to 39° C., preferably 37° C., for from 3 to 10 days, preferably 5 to 8 days, in the presence of a suitable medium. Desirably the medium is chemically defined with no biological additives, for example the medium is preferably serum-free. Such mediums as Eagle's Basel Medium (Eagle H., *Science,* (1959), 130, 432) or 199 Maintenance Medium (see Morgan, J. F. et al, *Proc. Soc. Exp.Biol.* (N.Y.), 73, 1, (1950), are suitable. Antibacterial agents such as penicillin and/or streptomycin may be added to the medium. After incubation the virus can be harvested by mechanical means such as freezing and thawing, and thereafter used for serially passaging in monolayer cultures of feline embryonic cells by standard tissue culture techniques (see "A Manual of Basic Virological Techniques" by G. C. Rovozzo and C. N. Burk, published by Prentice-Hall Inc., Eaglewood Cliffs, N.J. U.S.A 1973).

During the first few passages of the virus, usually up to 5 subcultures, no obvious cytopathic effect (C.P.E.) is visible. Thereafter FIP virus infection of cell monolayers causes the distinctive CPE described above, which appears after about 48 to 72 hours incubation. The cells eventually become detached from the surface of the culture vessel. The appearance of an obvious CPE determines the incubation time for each passage which may be from 1–5 days. The titre of virus produce from each passage will vary from between about $10^{4.0}$ TCID$_{50}$ and $10^{10.0}$ TCID$_{50}$ per ml. (TCID$_{50}$ means the tissue culture infective dose which produces a cytopathic effect in 50% of the culture cells exposed to virus.) After about the 100th passage the FIP virus may be considered as attenuated since it will stimulate the production of serum neutralising antibody in susceptible animals, without any significant side effects, and without causing the overt disease.

For large-scale production samples of the attenuated FIP virus, which is usually stored as a stock virus, are propagated on freshly prepared feline embryonic cell cultures, in an appropriate medium such as serum-free Eagle's Minimum Essential Medium, or 199 Maintenance Medium. When almost complete cytopathic effect becomes apparent after 1 to 5 days of incubation, the cells and medium are harvested. Each batch of virus so produced should be tested for sterility, potency, toxicity and the like according to the guidelines laid down by the British Pharmacopoeia (Veterinary) 1977 page 149. The virus suspension may then convenientkly be frozen in ampoules or vials, and stored in liquid nitrogen. Alternatively stabilizers such as sorbitol and/or protein hydrolysate, eg Sol-U-pro, may be added to enable the preparation to be freeze-dried.

In a further aspect of the invention there is provided a vaccine for developing immunity in animals to FIP, which comprises an attenuated FIP virus, as hereinbefore defined, in an effective dosage, or multiples thereof, in a pharmaceutically acceptable carrier. The effective dosage for vaccination may be from $10^{4.0}$ to $10^{8.0}$ TCID$_{50}$/ml, preferably $10^{5.0}$ to $10^{7.0}$ TCID$_{50}$/ml.

The pharmaceutically acceptable carrier for the vaccine can be a liquid, such as an aqueous solution containing nutrients and stabilizers, e.g. Hank's balanced salt solution or other similar media. The carrier may, in some instances, include a sterile sealed container, such as an ampoule or vial.

The vaccine of the present invention is administered to animals of the genus Felix desirably by intraperitoneal, subcutaneous, or intramuscular injection. or via the oral, nasal or intraocular route. The dose may be administered as a single dose or as a multiplicity of sub-doses over a period of time. The preferred schedule is to administer a single dose of 1–2 ml containing the effective dosage of attenuated FIP virus.

In addition to containing the attenuated FIP virus, the vaccine of the present invention may also contain other vaccines comprising antigenic material derived from other micro-organisms that cause disease in members of the genus Felix, such as parvovirus, e.g. feline panleucopenia (feline infectious enteritis), feline calicivirus, feline rabies, feline retrovirus, e.g. feline leukaemia virus, and feline herpes viruses. A particularly preferred combination, presented as a vaccine pack, comprises a wet preparation of attenuated FIP virus in a sterile vessel together with a vessel containing a freeze-dried preparation of one or more other feline vaccines, suitably adapted to be combined before usage.

Alternatively the attenuated FIP virus may be presented as a freeze-dried preparation, with the other vaccine(s) being presented in wet form. In yet a further alternative the attenuated FIP virus is freeze-dried in combination with one or more of the above mentioned vaccines and presented together with a vessel containing sterile water for use in reconstituting the freeze-dried vaccine prior to administration. The vessels are packaged in a box or container together with instructions for use, which include the instruction to reconstitute the freeze-dried vaccine with the wet preparation or sterile water prior to administration.

In a further aspect of the present invention there is provided a method for developing immunity in animals of the genus Felix to FIP which comprises the administration to the animal of an effective dosage of a vaccine as hereinbefore defined.

The following Examples illustrate the invention but do not limit it in any way.

EXAMPLE 1

Isolation and passaging of FIP virus recovered from peritoneal fluid of an infected cat Peritoneal fluid was removed aseptically from a 3 to 4 month old cat which had died from FIP, by pipette and inoculated on to confluent monolayers of diploid feline embryonic lung cells. Prior to inoculation the monolayers had been washed twice with phosphate buffered saline refed with serum free 199 Maintenance Medium.

The infected monolayers were inoculated at 37° C. for approximately 7 days after which time they were harvested by freezing and thawing. An aliquot of the medium and disrupted infected cells was then inoculated on to fresh monolayer cultures of diploid feline embryonic lung cells in 199 Medium, and incubated at 37° C.

After serially passaging the virus in a similar manner for 3 to 5 passes small areas of characteristic CPE started to appear, that is the infected cells produced irregular shapes and eventually rounded up, when viewed as wet preparations under the microscope. From the 5th passage onwards the CPE was very evident, and rapidly destroyed the cell sheet, i.e. within 48 to 72 hours.

The virus so obtained was serially passaged over 100 times producing titres ranging from $10^{4.0}$ TCID$_{50}$ to $10^{8.0}$ TCID$_{50}$/ml.

EXAMPLE 2

Isolation and passaging of FIP virus recovered from the liver of an infected cat The liver was removed from an 11 month old cat, which had died from FIP. The tissue was triturated in a tissue disintegrater, i.e. a Stomacher 80 (COLWORTH)

with phosphate buffered saline for 60 seconds. The suspension was then centrifuged at 1108 g after which the supernatant was decanted and inoculated on to confluent monolayers of diploid feline whole embryo cells in serum free 199 Medium and incubated at 37° C. for 7 days.

The virus was then harvested and passaged as described in Example 1, with an identical CPE being produced at each passage.

EXAMPLE 3

Isolation and passaging of FIP virus recovered from the blood of an infected cat at the acute stage of the disease A 6 months old cat suffering from FIP, as demonstrated by pyrexia and loss of condition, was bled from the jugular vein. The blood was left for 20 minutes to allow it to clot. The serum/plasma was removed friom the clot, the clot was then triturated in a tissue disintegrater, i.e. a Stomacher, in phosphate buffered saline for 60 seconds. The suspension was then centrifuged at 1108 g after which the supernatant was decanted and used to inoculate confluent monolayers of diploid feline embryonic lung cells in serum free 199 Medium and incubated at 37° C. for 5 to 8 days.

The virus was then harvested and passaged as described in Example 1, with CPE being produced at each passage.

EXAMPLE 4

The virus obtained from Example 2 was passaged in a heteroploid feline embryonic lung cell line prepared according to the method described in U.K. Pat. No. 1 286 250 (a heteroploid cell line is formed when cells have been passaged successfully more than 70 times from primary culture and have in consequence become an established cell line). A CPE was produced which was identical to that described in Example 1. The titre of virus produced ranged again between $10^{4.0}$ and $10^{10.0}$ $TCID_{50}$/ml.

EXAMPLE 5

The cells from the 100th passage described in Example 1 were harvested by freezing and thawing to provide an attenuated FIP vaccine. The vaccine so prepared was administered to 12 week old cats, which had previously been shown to be free of FIP antibodies, by intra-peritoneal injection as a single dose of 2 ml containing $10^6$ $TCID_{50}$/ml of virus. After 21 days the cats were bled and sera examined for the presence of neutralising antibody. Significant levels of neutralising antibody were found to be present as was demonstrated below:

| | |
|---|---|
| Pre-vaccination antibody titre = | <10 |
| Post-vaccination antibody titre = | 160 |

EXAMPLE 6

A vaccine pack for immunising members of the genus Felix against FIP, feline infectious enteritis (FIE) and feline rabies is composed of a vial containing a freeze-dried preparation of live attenuated FIP vaccine as prepared in Example 1 and live attenuated FIE vaccine, and a second vial containing an inactivated rabies virus suspension, together with instructions to reconstitute the freeze-dried vaccine with the wet preparation prior to administration.

EXAMPLE 7

A vaccine peak for immunising members of the genus Felix against FIP, feline infectious enteritis (FIE) and feline viral rhinotracheitis is composed of a vial containing a freeze-dried preparation of live attenuated FIP vaccine as prepared in Example 1 and live attenuated FIE vaccine, and a second vial containing a suspension of live modified feline viral rhinotracheitis, together with instructions to reconstitute the freeze-dried vaccine with the wet preparation prior to administration.

We claim:

1. An attenuated feline infectious peritonitis virus which stimulates production of antibody in susceptible animals, without causing symptoms characteristic of feline infectious peritonitis, which morphalogically resembles a corona virus which is the causative virus of avian infectious bronchitis (AIB), whilst differing from the AIB virus in as much as it is capable of growing in mammalian tissue culture but not in embryonating eggs and which on infecting tissue culture cells causes them to produce irregular shapes, when examined microscopically as wet preparations, and ultimately roundup and/or become detached from the solid surface on which they are growing, said virus resulting from at least 100 passages of a virulent feline infectious peritonitis virus in feline embrionic cell cultures.

2. The virus according to claim 1 wherein said virus is essentially spherical in shape with a diameter of 80 to 160 mm. and has outstanding projections approximately 25 mm. long.

3. An attenuated strain of feline peritonites virus prepared by serially passaging virulent feline peritonitis virus, isolated from the peritoneal fluid, blood, urine or various organs of a cat suffering from the disease, in susceptible feline embryonic heteroploid cell line, or diploid cell strain cultures at least 100 times.

* * * * *